United States Patent [19]

Stevenson

[11] 4,199,578

[45] Apr. 22, 1980

[54] COMPOSITION

[75] Inventor: Neil A. Stevenson, Loughborough, England

[73] Assignee: Fisons Limited, London, England

[21] Appl. No.: 963,814

[22] Filed: Nov. 27, 1978

[30] Foreign Application Priority Data

Nov. 30, 1977 [GB] United Kingdom ............... 49759/77

[51] Int. Cl.² ............................................. A61K 31/56
[52] U.S. Cl. .................................................... 424/240
[58] Field of Search ......................................... 424/240

[56] References Cited

U.S. PATENT DOCUMENTS 3,845,085  10/1974  Phillipps et al. ................. 260/397.45

FOREIGN PATENT DOCUMENTS 1429184  3/1976  United Kingdom ..................... 424/241

*Primary Examiner*—Elbert L. Roberts
*Attorney, Agent, or Firm*—Merriam, Marshall & Bicknell

[57] ABSTRACT

There is described a pharmaceutical composition comprising a mixture of particulate beclomethasone dipropionate, at least 90% by weight of the particles of beclomethasone dipropionate having an effective particle size below 10 micrometers, and a powder carrier, preferably in the absence of free liquid.

The compositions are indicated for use in the treatment of asthma or hay fever.

19 Claims, No Drawings

COMPOSITION

This invention concerns pharmaceutical powder compositions which may be dispersed from a container, for example by means of an inhalation device, into the inhaled air stream. Many such devices are known, e.g. those described in United Kingdom Pat. Specification No. 1,122,284 and Belgian Patent Specification No. 851,241.

Medicaments for administration by inhalation should be of a controlled particle size in order to achieve maximum penetration into the lungs, a suitable particle size range being 0.01–10, usually 1–10, micrometers. However, powders in this particular size range are not readily fluidised and dispersed by means of known inhalation devices because of cohesive forces between the individual particles. It is also desirable to use fine particles of drug for administration to the nose.

Beclomethasone dipropionate has for a number of years been sold as a pressure pack formulation containing chlorofluorinated hydrocarbon propellants and various other excipients. The long term toxicological and enviornmental effects of these propellants and excipients are however not well known. Furthermore many patients, especially children, find pressure pack formulations of beclomethasone dipropionate difficult to use effectively.

We have now found that beclomethasone dipropionate can be formulated in a suitable manner for administration to the nose and/or lungs by admixture with a non-toxic and a simple or naturally occuring carrier. The compositions of the present invention provide a simple and safe means of administering beclomethasone dipropionate to the nose or lungs and provide a convenient and safe means of exploiting the use of this compound in the treatment of these organs, e.g. the treatment of asthma or hay fever.

According to the invention therefore we provide a pharmaceutical composition comprising a mixture of particulate beclomethasone dipropionate, at least 90% by weight of the particles of beclomethasone dipropionate having an effective particle size below 10 micrometers, and a powder carrier, preferably in the absence of free liquid. The dry powder carrier is preferably lactose.

According to a preferred feature the invention provides a pharmaceutical powder composition, which comprises a mixture of beclomethasone dipropionate, at least 90% by weight of the particles of which have an effective particle size below 10 micrometers (and preferably of from 0.01 to 10 micrometers), and a carrier acceptable in the nose or lung, at least 90% by weight of the particles of the carrier having an effective particle size below 400 micrometers, and at least 50% by weight of the particles of the carrier having an effective particle size about 30 micrometers.

Effective particle size for particles below 30 micrometers may be measured by a Coulter counter.

In measuring particle sizes with a Coulter counter, the sample to be analysed is dispersed in an electrolyte into which dips a glass tube. The glass tube has a hole through the wall thereof with electrodes mounted on either side of the hole in the tube wall. The tube is immersed sufficiently for the hole and electrodes to be submerged in the liquid. The suspension is made to flow through the hole in the glass tube and as each particle passes through the orifice it displaces its own volume of electrolyte, thus changing the resistance across the hole. This change in resistance is converted into a voltage pulse with an amplitude proprotional to the particle volume. The pulses are fed to an electronic counter with an adjustable threshold level such that all pulses above the threshold are counted. By setting the threshold level at different values it is possible to determine the number of particles falling within given size ranges and thus the proportion of particles in a sample which fall outside a desired particle size range. Effective particle size for particles above 30 micrometers may be measured by air jet sieving using the 'air jet sieve 200' made by the Alpine Machine and Steel Works, Gögginger Landstrasse 66, 89 Augsburg, West Germany.

Desirably, at least 95% by weight of the particles of the beclomethasone dipropionate have an effective particle size in the range 0.01 to 10 micrometers. Preferably at least 90%, and more desirably at least 95% by weight thereof have an effective particle size in the range 1 to 10 micrometers. Suitably, at least 50% by weight of the particles of beclomethasone dipropionate have an effective particle size in the range 2 to 6 micrometers.

The particle size spectrum of the carrier will depend on the particular inhalation device from which the formulation is to be dispersed. It is however desirable (but not absolutely necessary or indeed practically possible), to avoid particles of less than 10 micrometers in size, thus minimising the number of non-drug particles which penetrate deep into the lung. A large proportion of very large particles can also cause a gritty feel in the mouth of the user and is therefore less preferred. Use of a carrier of large particle size may also cause problems in filling when using filling machines which involve a dosator which picks up powder by dipping into a powder bed from above. However use of a carrier of large particle size may ease filling when using machines in which a die is filled from above, but may incline the composition to segregate during transport or storge. Thus desirably, at least 95% by weight of the particles of carrier have an effective particle size below 400 micrometers. Preferably at least 50%, and more desirably at least 70%, by weight of the carrier particles have an effective particle size in the range 30 to 150, especially 30 to 80, micrometers.

The composition preferably contains from 0.01 to 2% by weight, more especially from 0.01 to 1% by weight, and particularly from 0.01 to 0.5% by weight of the beclomethasone dipropionate, and from 99.99 to 98% by weight, more especially from 99.99 to 99% by weight, and particularly from 99.98 to 99.5% by weight of the carrier.

The finely divided beclomethasone dipropionate may be prepared in the desired particle size range for example using a ball mill, a fluid energy mill or precipitation. The carrier may be prepared by grinding and subsequently separating out the desired fraction, for example by air classification and/or sieving.

The compositions may be prepared by mixing the ingredients together in one or, preferably, more (e.g. two) steps in a mixer, such as a planetary or other stirred mixer. The invention thus also provides a method for preparing a composition of the invention, which comprises mixing together the beclomethasone dipropionate and the carrier, after comminution and classification of the ingredients if this is necessary or desired.

The carrier may be any non-toxic material which is chemically inert to the beclomethasone dipropionate and will of course be acceptable for inhalation or for administration to the nose. Examples of carriers which may be used include inorganic salts, e.g. sodium chloride or calcium carbonate; organic salts, e.g. sodium tartrate or calcium lactate; organic compounds, e.g. urea or propylidone; monosaccharides, e.g. lactose, mannitol, arabinose or dextrose monohydrate; disaccharides, e.g. maltose or sucrose; polysaccharides, e.g. starches, dextrins or dextrans. A particularly preferred carrier is lactose, e.g. crystalline lactose.

In addition to the beclomethasone dipropionate and carrier, the composition may contain other ingredients, such as colouring matter or flavouring agents such as saccharine, which are normally present in inhalent compositions. It is, however, preferred to use the minimum of such other ingredients and that, when present, at least 90% by weight of the particles thereof should have an effective particle size in the range 30–150 micrometers.

In addition to the above ingredients the composition may contain a bronchodilator, e.g. isoprenaline, rimiterol, ephedrine, ibuterol, isoetharine, fenoterol, carbuterol, clinbuterol, hexaprenaline, salmifamol, soterenol, trimetoquinol or a pharmaceutically acceptable salt of any one thereof, or preferably orciprenaline, terbutaline or salbutamol or a pharmaceutically acceptable salt of any one thereof.

The bronchodilator preferably has an effective particle size similar to that of the beclomethasone dipropionate. The amount of bronchodilator used may be the same as, or less than, that which is normally used for inhalation application of the particle bronchodilator concerned.

According to a further feature of the invention therefore we provide a pharmaceutical composition, comprising a mixture of beclomethasone dipropionate and a bronchodilator, the beclomethasone diproprionate and the bronchodilator preferably both having an effective particle size of from 0.01 to 10 micrometers and the mixture also preferably comprising a coarse carrier as described above.

The compositions according to the invention will generally be put up in sealed gelatine, plastic or other capsules.

There is also provided, therefore, as a further feature of the invention, a dosage unit comprising a gelatine or like capsule containing beclomethasone dipropionate, preferably in the form of a pharmaceutical composition of the present invention.

The amount of composition contained in the capsule will, of course, to some extent depend on the desired dosage. However, the capsule suitably contains from 10 to 400, and preferably 20 to 200, e.g. 50, 100 or 150 micrograms of the beclomethasone dipropionate. Each capsule desirably contains from 10 to 50, and more preferably 20 to 50 mg of the composition.

From another aspect the invention also provides a capsule, cartridge or like container, the container being loosely filled to less than about 80% by volume, preferably less than about 50% by volume, with a composition according to the invention. The composition should of course not be compacted into the container.

The capsules should preferably be designed to protect their contents from light, e.g. they should be opaque, or the capsules may be packed and/or stored in opaque containers, e.g. cans or opaque or coloured bottles, or metal foil.

The compositions according to the invention are useful in the treatment of asthma and hay fever. Thus unit doses of the composition each containing, e.g. 20 to 200 micrograms of beclomethasone dipropionate, may be administered by means of a suitable powder inhaler to a patient suffering from asthma. In the treatment of hay fever the powder is preferably administered directly to the nose.

The invention is further described in the following Examples, which are given merely by way of illustration.

EXAMPLE 1

Preparation of Adult's Dosage Unit

Formula for 25 kg batch size:

Beclomethasone Dipropionate (less than 10 micrometers effective particle size) 100g.

Appropriately classified Lactose (e.g. Lactose which has passed through a 200 micrometer sieve) to 25 kg.

Add the following, in the order stated, to a high speed dry disperser of suitable size.
1. Classified Lactose 500 g,
2. Beclomethasone Dipropionate 100 g,
3. Classified Lactose 500 g.

Run disperser for a length of time to effect a random mixture, usually 5–10 minutes.

Transfer this pre-mix into a suitably sized dry disperser and add the remainder of the classified lactose.

Run the machine until a random mixture is achieved, usually 10–15 minutes.

Fill suitably sized unit containers, usually gelatin shells, with 25 mg of the mixture (100 microgrammes of beclomethasone dipropionate). Very little or no compression should be used on the mixture during the filling operation.

The unit doses should be packed to protect them from light, e.g. in an amber glass bottle or in a multiple or unit dose aluminium foil sachet.

Unit doses containing 150 microgrammes of beclomethasone dipropionate may be made in a similar manner.

EXAMPLE 2

Preparation of Child's Dosage Unit

Formula for 25 kg batch size:

Beclomethasone Dipropionate (less than 10 micrometers effective particle size) 50g.

Appropriately classified Lactose (e.g. Lactose which has passed through a 200 micrometer sieve) to 25 kg.

Add the following in the order stated to a high speed dry disperser of suitable size.
1. Classified Lactose 500 g,
2. Beclomethasone Dipropionate 50 g,
3. Classified Lactose 500 g.

Run disperser for a length of time to effect a random mixture, usually 5–10 minutes.

Transfer this pre-mix into a suitably sized planetary mixer or drum roller, containing a baffle, which gyrates. Add the required classified lactose to make up the batch.

Run the mixer until a random mixture is achieved, usually 20–30 minutes.

Fill and pack as described in Example 1.

A suitable lactose for use in the formulations of the invention has the following sieve analysis.

|  | % by weight |
|---|---|
| Retained on 210 micron sieve | 0–5 |
| Passing 210 micron retained on |  |

-continued

|  | % by weight |
|---|---|
| 125 micron sieve | 15–30 |
| Passing 125 micron retained on 89 micron sieve | 15–25 |
| Passing 89 micron retained on 53 micron sieve | 25–35 |
| Passing 53 micron sieve | 20–35 |

I claim:

1. A pharmaceutical composition for inhalation therapy, comprising a mixture of particulate beclomethasone dipropionate, at least 90% by weight of the particles of beclomethasone dipropionate having an effective particle size below 10 micrometers, and a powder carrier of effective particle size for administration of said composition by inhalation.

2. A composition according to claim 1, which comprises a mixture of beclomethasone dipropionate, at least 90% by weight of the particles of which have an effective particle size below 10 micrometers, and a carrier acceptable in the nose or lung, at least 90% by weight of the particles of the carrier having an effective particle size below 400 micrometers, and at least 50% by weight of the particles of the carrier having an effective particle size above 30 micrometers.

3. A composition according to claim 2, wherein at least 90% by weight of the particles of beclomethasone dipropionate have an effective particle size in the range 1 to 10 micrometers and at least 50% by weight of the particles of beclomethasone dipropionate have an effective particle size in the range 2 to 6 micrometers.

4. A composition according to claim 2, wherein at least 95% by weight of the particles of carrier have an effective particle size below 400 micrometers.

5. A composition according to claim 4, wherein at least 50% by weight of the carrier particles have an effective particle size in the range 30 to 150 micrometers.

6. A composition according to claim 5, wherein at least 50% by weight of the carrier particles have an effective particle size in the range 30 to 80 micrometers.

7. A composition according to claim 1, comprising from 0.01 to 2% by weight of beclomethasone dipropionate.

8. A composition according to claim 7, comprising from 0.01 to 1% by weight of beclomethasone dipropionate.

9. A composition according to claim 8, comprising from 0.02 to 0.5% by weight of beclomethasone dipropionate.

10. A composition according to claim 1, wherein the carrier is lactose.

11. A composition according to claim 1 comprising a bronchodilator.

12. A composition according to claim 11, wherein the bronchodilator is orciprenaline, terbutaline or salbutamol or a pharmaceutically acceptable salt of any one thereof.

13. A composition according to claim 1 in a sealed capsule.

14. A capsule containing from 10 to 50 mg of a composition according to claim 1.

15. A capsule loosely filled to less than 80% by volume with a composition according to claim 1.

16. A composition according to claim 1 packed in an opaque container.

17. A capsule containing beclomethasone dipropionate in unit dosage form.

18. A pharmaceutical composition for inhalation therapy, comprising a mixture of beclomethasone dipropionate and a bronchodilator.

19. A method of treatment of asthma or hay fever which comprises inhalation administration of a composition according to claim 1 to a patient suffering from asthma or hay fever.

* * * * *

UNITED STATES PATENT AND TRADEMARK OFFICE
CERTIFICATE OF CORRECTION

PATENT NO. : 4,199,578
DATED : April 22, 1980
INVENTOR(S) : Neil A. Stevenson

It is certified that error appears in the above-identified patent and that said Letters Patent are hereby corrected as shown below:

Column 1, line 15, "particular" should be --particle--.

Column 1, line 24, "enviornmental" should be --environmental--.

Column 1, line 57, "about" should be --above--.

Column 2, line 47, "0.01" should be --0.02--.

Column 3, line 14, "inhalent" should be --inhalant--.

Column 3, line 31, "particle" should be --particular--.

Signed and Sealed this

First Day of July 1980

[SEAL]

Attest:

SIDNEY A. DIAMOND

Attesting Officer     Commissioner of Patents and Trademarks